United States Patent

Shen et al.

[11] Patent Number: 5,573,648
[45] Date of Patent: Nov. 12, 1996

[54] GAS SENSOR BASED ON PROTONIC CONDUCTIVE MEMBRANES

[75] Inventors: Yousheng Shen; Franco Consadori, both of Salt Lake City; D. George Field, Pleasant Grove, all of Utah

[73] Assignee: Atwood Systems and Controls, Salt Lake City, Utah

[21] Appl. No.: 381,718

[22] Filed: Jan. 31, 1995

[51] Int. Cl.6 .................................................. G01N 27/407
[52] U.S. Cl. ........................ 204/412; 204/421; 204/424; 204/425; 204/426; 205/781; 205/783.5; 205/784; 205/786.5; 205/788
[58] Field of Search ................................... 204/421–429, 204/412

[56] References Cited

U.S. PATENT DOCUMENTS

| | | | |
|---|---|---|---|
| 4,024,036 | 5/1977 | Nakamura et al. | 204/427 |
| 4,227,984 | 10/1980 | Dempsey et al. | 204/430 |
| 4,536,274 | 8/1985 | Papadakis et al. | 204/433 |
| 4,664,757 | 5/1987 | Zupancic et al. | 204/426 |
| 5,118,398 | 6/1992 | McElroy et al. | 204/153.1 |
| 5,133,857 | 7/1992 | Alberti et al. | 204/425 |
| 5,164,053 | 11/1992 | Razaq et al. | 204/153.18 |
| 5,173,166 | 12/1992 | Tomantschger et al. | 204/412 |
| 5,302,274 | 4/1994 | Tomantschger et al. | 204/412 |

OTHER PUBLICATIONS

Sung B. Lee, Anthony Cocco, Darioush Keyvani and G. Jordan Maclay, *Humidity Dependence of Carbon Monoxide Oxidation Rate in a Nafion–Based Electrochemical Cell*, vol. 142, No. 1, Jan. 1995.

*Primary Examiner*—T. Tung
*Attorney, Agent, or Firm*—Workman Nydegger & Seeley

[57] ABSTRACT

A low cost room temperature electrochemical gas sensor for sensing CO and other toxic analyte gases has a solid protonic conductive membrane with a low bulk ionic resistance. A sensing electrode and a count counter electrode, which are separated by the membrane, can be made of mixed protonic-electronic conductors. Embodiments of the inventive sensor also include an electrochemical analyte gas pump to transport the analyte gas away from the counter electrode side of the sensor. Analyte gas pumps for the inventive sensor include dual pumping electrodes situated on opposite sides of the membrane, and include a means for applying a DC power across the membrane to the sensing and counter electrodes. Another embodiment of the inventive sensor has first and second solid protonic conductive membranes, one of which has a sensing electrode and a counter electrode separated by the first membrane, and the other of which has dual pumping electrodes situated on opposite sides of the second membrane.

78 Claims, 7 Drawing Sheets

GAS SENSOR BASED ON PROTONIC CONDUCTIVE MEMBRANES

FIELD OF THE INVENTION

The invention relates to electrochemical gas sensors, and particularly relates to electrochemical gas sensors having a sensing electrode, a counter reference electrode, and a solid proton conductor for room temperature detection of the concentration of carbon monoxide (CO) in the ambient.

BACKGROUND OF THE INVENTION

In most prior art solid state commercial gas sensors, it is necessary to heat the sensor element to elevated temperatures in order to acquire both fast response time and high sensitivity to objective gases. For example, N-type semiconductor tin oxide gas sensors and catalytic combustion type Pd/Pt gas sensors must usually be operated in a temperature range of ca. 200° to 500° C. These sensors must be equipped with heaters connected to external power sources. Therefore, room temperature CO gas sensors, which use less power, are desirable.

It is well known that CO reacts with moisture in air at room temperature, and forms protons, electrons, and CO2 in an oxidation reaction of CO.

$$CO + H_2O \rightarrow CO_2 + 2H^+ + 2e^- \quad (1)$$

It is also known that there is a moisture formation reaction by combining protons, electrons, and oxygen in a reduction reaction of oxygen:

$$2H^+ + 2e^- + \tfrac{1}{2}O_2 \rightarrow H_2O \quad (2)$$

These two reactions are the basis of prior art room temperature low power electrochemical gas sensors utilizing a proton conductor. FIG. 1 shows the transport processes of such a CO gas sensor. A protonic conductor 12 conducts ionized hydrogen atoms from a sensing electrode 16 where the sensor signal originates from the oxidation reaction of carbon monoxide at sensing electrode 16. Ionized hydrogen atoms, each of which constitutes a single proton, are conducted through protonic conductor 12 to a counter electrode 14. Electrons that are liberated in the oxidation of carbon monoxide at sensing electrode 16 are conducted through an electrical lead 22 to voltage meter 18, through an electrical lead 20, and to counter electrode 14 for a reduction reaction of oxygen. In a steady state reaction, the hydrogen ions are transported from sensing electrode 16 to counter electrode 14 in the depicted potentiometric CO gas sensor.

The current generated by the reactions depicted in FIG. 1 can also be measured by an amp meter 24 having a resistor $R_L$ 26, which circuit represents a transport process of an amperometric CO sensor. Absent amp meter 24, resistor $R_L$ 26, the leads thereto which are shown in phantom, transport processes of a potentiometric CO gas sensor are shown for voltage meter 18 and leads 20, 22.

Whether the transport processes shown in FIG. 1 are for potentiometric CO gas sensor or for an amperometric CO sensor, electrons from the process of the oxidation reaction of carbon monoxide travel as seen in arrow 21 in FIG. 1 through leads 20, 22.

The sensor of FIG. 1 is operated in a current mode when the sensing and counter electrodes 16, 14 are connected to each other through load resistor $R_L$, or are connected to a DC power source (not shown) which electrically drives the protons across proton conductor 12.

A prior art room temperature proton conductor sensor developed by General Electric using a polymer porous support material saturated by a liquid proton conductor, has been constructed as an electrochemical amperometric CO gas sensor (the G. E. Sensor). In the G. E. Sensor, a liquid reservoir was used to provide the liquid proton conductor to the porous support material. Protons, which are indicative of the ambient CO concentration, were driven across the porous support material through the liquid conductor by a DC voltage. Electrical current response of the sensor to ambient CO concentration was linear. The cost of the sensor with such a complicated design, however, is high and is thus not be suitable for practical consumer applications.

In U.S. Pat. No. 4,587,003, a room temperature CO gas sensor using a liquid proton conductor is taught. Basically, the mechanism and design of the sensor were similar to the G. E. sensor, except that the outside surfaces of the sensing and counter electrodes of the sensor in this patent were coated by porous NAFION™ layers. The CO room temperature gas sensor taught in the patent currently costs about $200.00. The lifetime of such a sensor is about 6–12 months due to the rapid drying of the liquid of the electrolytes. In addition, the sensor requires maintenance due to leakage and corrosion of liquid electrolyte.

The discovery of room temperature solid proton conductors aroused considerable efforts to investigate low cost, all-solid electrochemical room temperature CO gas sensors. One such sensor that was developed was a room temperature CO gas sensor with a tubular design using proton conductors, electronically conductive platinum or the like as the sensing electrode, and electronically conductive silver, gold, graphite or the like as the counter electrode. The sensing electrode decomposed carbon monoxide gas to produce protons and electrons, whereas the counter electrode exhibited no activity to decompose carbon monoxide with the result that a Nernst potential occurred between the two electrodes. Thus, carbon monoxide gas was detected.

In detecting carbon monoxide with the tubular design sensor, protons and electrons are generated at the sensing electrode. For the reaction to be continued, protons and electrons must be removed from the reaction sites, and CO and moisture must be continuously provided from the gaseous phase to the reaction sites. Therefore, the CO reaction only occurs at three-phase contact areas. The three-phase contact areas consist of the proton membrane phase, the platinum electron phase, and the gas phase. Due to the limited three-phase contact areas in the tubular design sensor, the CO reaction was slow. Additionally, the response signal was weak. Further, the Nernst potential was not zero in clean air.

A modified electrochemical CO room temperature gas sensor using a planar or tubular sensor design was a subsequent development to the earlier tubular design CO sensor. In order to overcome the problem that the Nernst potential is not zero in clean air experienced with the earlier tubular design CO sensor, the improved design proposed a four probe measurement method for CO gas detection. The improved design achieved a zero reading in clean air, and the improved sensor was insensitive to variations in relative humility. Theoretical analysis based on electrochemistry, however, indicates that there is no difference between the four probe method and the normal two probe method of the earlier tubular design CO sensor. The improved sensor still used electronic conductors for both the sensing and counter electrodes, and showed slow and weak response signals to CO gas.

A still further improved design of a CO sensor is a room temperature electrochemical gas sensor using a solid polymer proton conductor with a planar sensor design. Response of this further improved sensor to CO was very weak, and was in the nA range even as a DC power source was applied. Apparently, the internal resistance of the sensor was too large. Calculations based on this further improved sensor dimensions indicates that the ionic resistance of the proton conductor membrane is about 400 K-ohm, which is too large to generate a usably strong signal. Further development and improvement of the planar CO gas sensor, which incorporated a sensing mechanism, resulted in performance that was still in nA range of sensor response.

SUMMARY AND OBJECTS OF THE INVENTION

It is an object of this invention to provide a low cost room temperature electrochemical gas sensor, for carbon monoxide and other toxic gases, having a low ionic resistance, a rapid response, and a strong signal to the detection of gaseous CO in the ambient. The toxic gases that can be sensed by the inventive sensor, each of which is referred to herein as an analyte gas, include $H_2$, $H_2S$, $H_2O$ vapor, and $NO_x$ concentrations.

The inventive electrochemical sensor has both a sensing electrode and a counter electrode. Each of the sensing and counter electrodes can be made of mixed protonic-electronic conductors so as to encourage a high surface area for reactions at the electrodes, which cause fast analyte gas reaction kinetics and a continuity in the transport of electrical charges so as to avoid polarization effects at the electrodes, thus achieving a fast and strong signal response by the sensor in the presence of the analyte gas.

A further aspect of the inventive gas sensor is that only two electrodes are required, whereas prior art gas sensors require three electrodes and a DC power supply.

These objects have been achieved by using a novel button sensor design, which may include mixed proton-electron conductive electrodes, various embodiments of which may also include an electrochemical analyte gas pump to transport analyte gas away from the counter electrode side of the gas sensor. While the inventive sensor is referred to herein as a CO sensor, it is contemplated that the inventive sensor is also capable of sensing other toxic analyte gases disclosed herein.

These and other objects and features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by counter-reference to specific embodiments thereof which are illustrated in the appended drawings. Understanding that these drawings depict only a typical embodiment of the invention and are not therefore to be considered to be limiting of its scope, the invention will be described and explained with additional specificity and detail through the use of the accompanying drawings in which:

FIG. 2 also sets forth optional electrical switching circuitry that enables intermittent CO pumping away from the counter electrode alternating with direct sensing of CO through the switch mechanism. Without such switching circuitry, the inventive electrochemical CO sensor depicted in FIG. 2 continuously senses CO.

The purpose of a CO electrochemical pump is to prevent an accumulation at the counter electrode of the inventive CO sensor. The CO pump lends increases stability to the sensor response in that the sensor response has less of a propensity to shift with time as in prior art CO sensing devices. When DC power is used as the motivator for the electrochemical CO pump, the passing of electrons from the sensing electrode to the reference electrode is enhanced. By reversing the DC power, the CO is kept away from the reference electrode and does not cause a buildup of CO on the back side of the sensing electrode.

Figure 2:
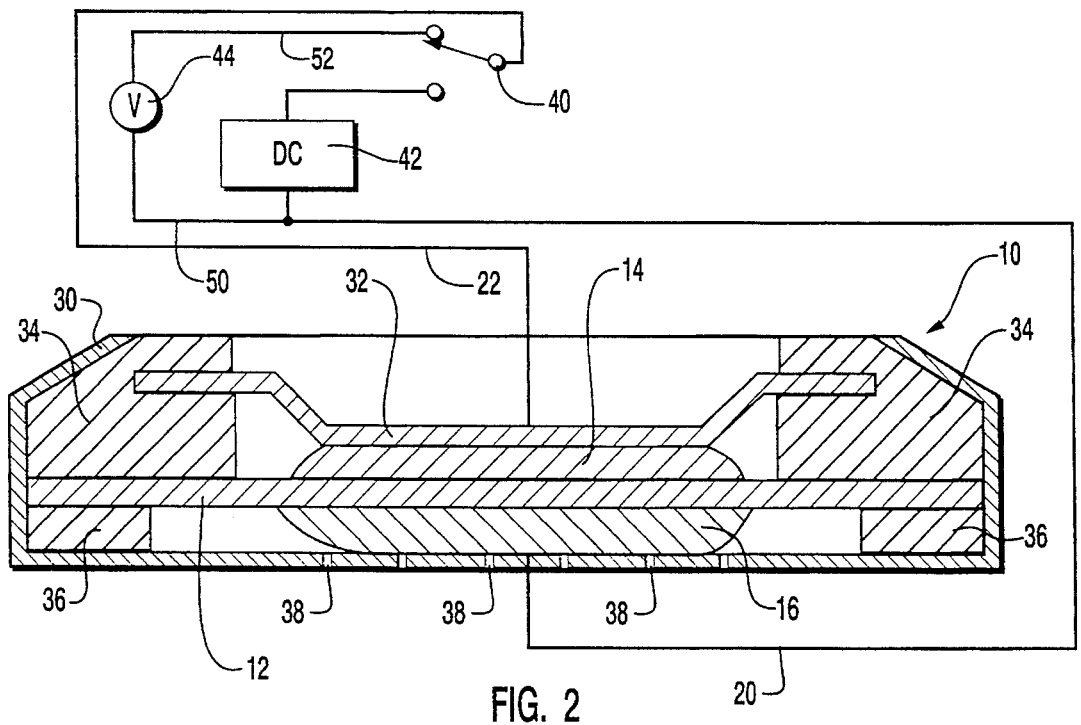
FIG. 2 shows an embodiment for the inventive electrochemical gas sensor that is contained in a can having a cap which encloses a counter electrode and a sensing electrode, where a protonic conductor is situated between the electrodes, which electrodes are separated by insulated packing material within the can and cap container arrangement.
Figure 3A:
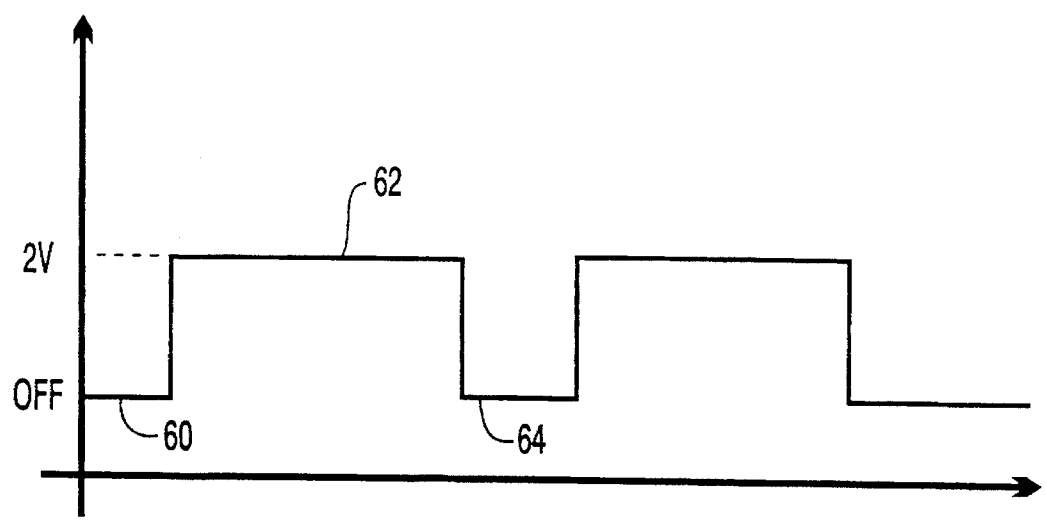
Figure 3B:
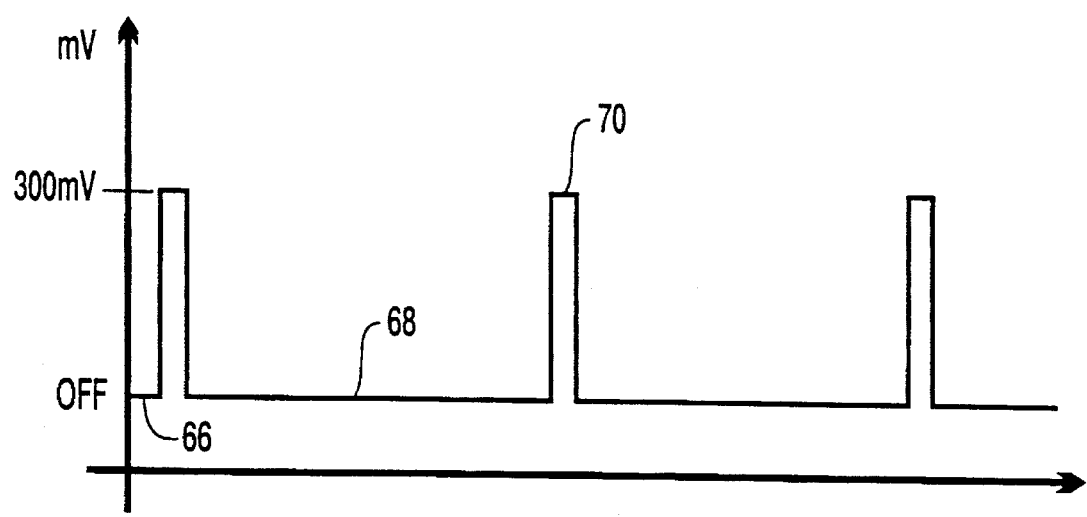

FIGS. 3A and 3B respectively depict sensor output where CO is intermittently pumped away from the counter electrode depicted in FIG. 2 when the switching circuitry therein is activated, where a DC pulse power is applied across the protonic conductive membrane to pump CO, and the sensing response is recorded when the DC pulse power is not applied across the protonic conductive membrane. When the DC pulse power is applied, permeated CO gas is catalytically converted to protons and then is pumped out of the reference electrode side of the inventive electrochemical sensor depicted in FIG. 2.

Figure 4:
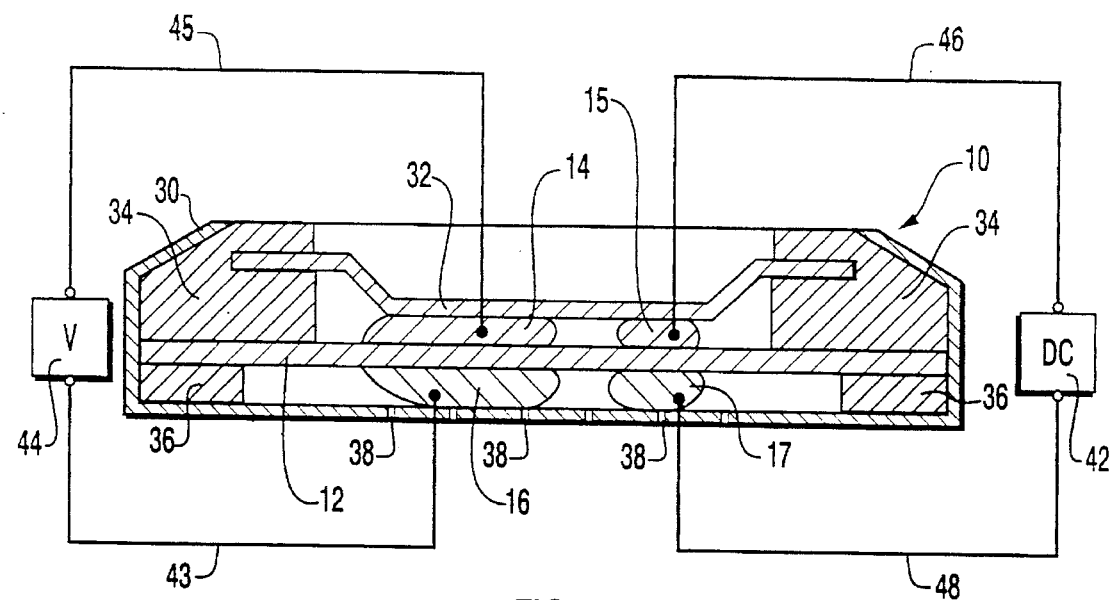

FIG. 4 shows an alternative embodiment of the inventive electrochemical sensor, further featuring a CO pump structure. The electrochemical sensor depicted in FIG. 4 has four electrodes attached to a protonic conductive membrane, two of which are normal sensing and counter electrodes, and the other two electrodes are used to pump permeated CO out of the counter electrode side of the electrochemical cell. In this alternative embodiment of the inventive CO sensor, DC power can be applied in either a pulse mode or a constant mode. The electrochemical sensor 15 is enclosed within an electrically insulated cap and can design.

Figure 5:
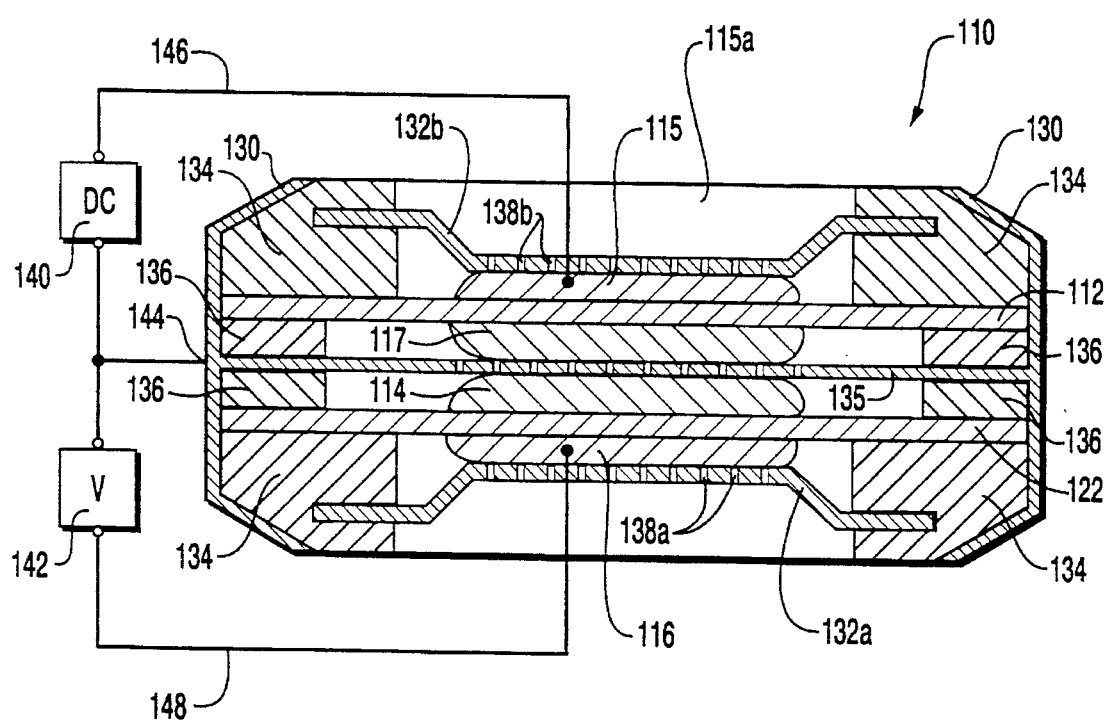

FIG. 5 shows a further embodiment of the inventive electrochemical CO sensor, having two protonic conductive membranes, the first membrane being used to sense CO, and the second membrane being used to pump permeated CO out of the counter electrode side of the electrochemical CO sensor.

Figure 6A:
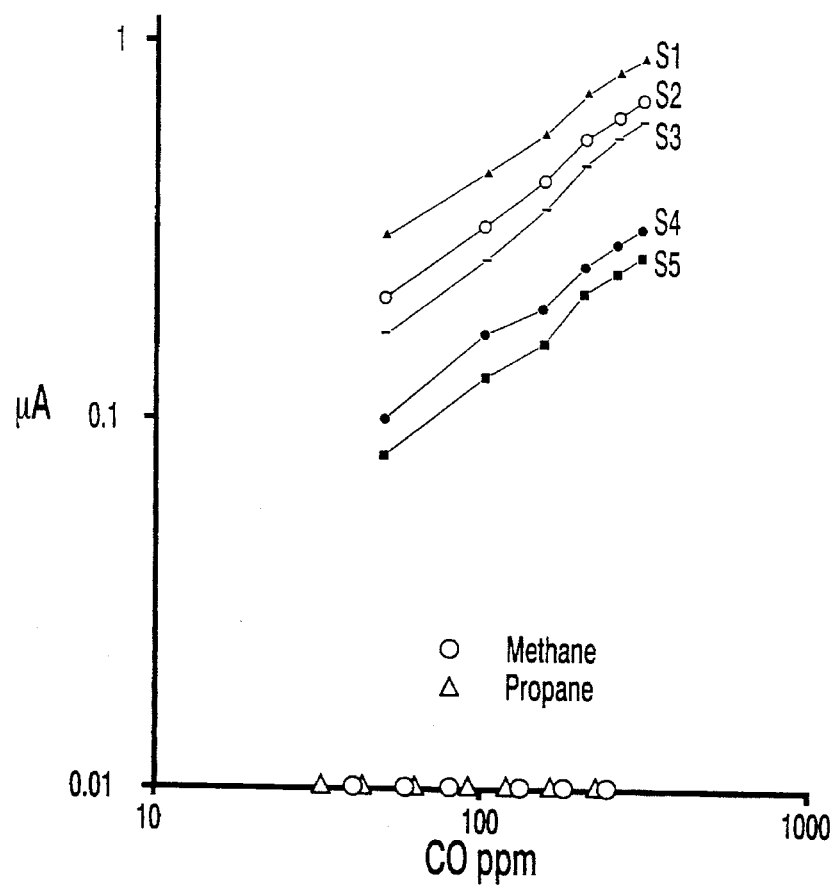

FIG. 6A shows five sensor current signal responses in environmental parameters of 22° C. and 20% relative humidity, as measured in current versus CO concentration, where sensors having a larger size show a higher current responses.

FIG. 6A also shows current signal response for varied concentrations of methane and propane, to demonstrate that sensor response is not interfered with by increasing concentrations of methane and propane.

Figure 6B:
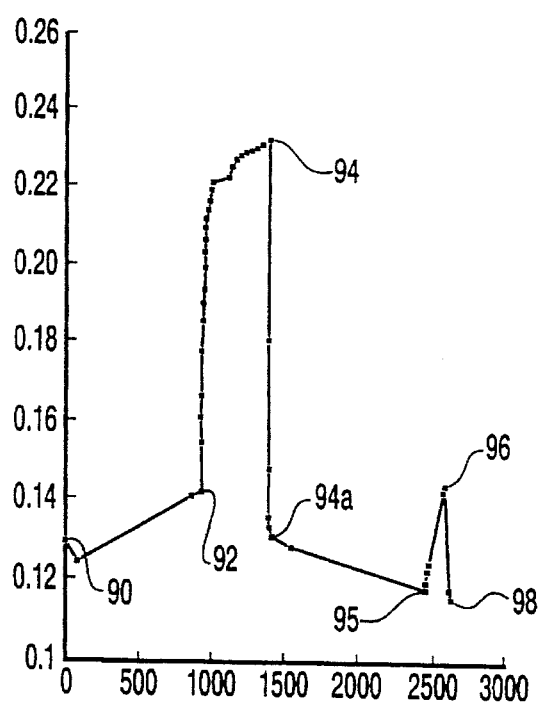

FIG. 6B shows sensor response with respect to time for varying concentrations of carbon monoxide in an environment of 19°–24° C., and relative humidity from 23–29%. FIG. 6B shows voltage signal response of a two membrane sensor similar to that depicted in FIG. 5.

Figure 7:
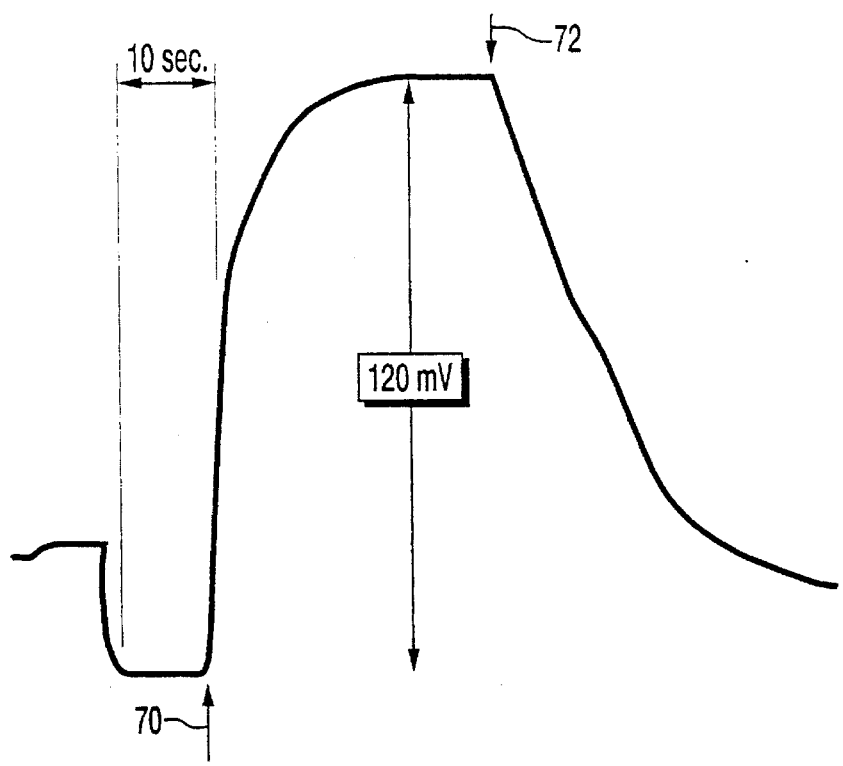

FIG. 7 shows a graph of voltage signal response as a function of time for an embodiment of the inventive electrochemical CO sensor in an environment of varying CO concentration.

Figure 8:
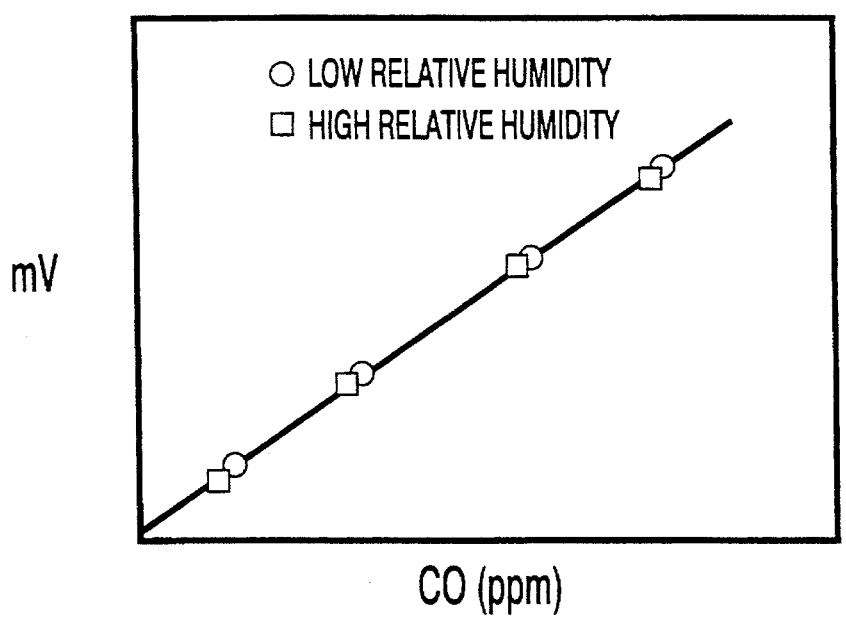

FIG. 8 shows a plot of sensor voltage signal response versus CO concentration at dual relative humidities.

Figure 9:
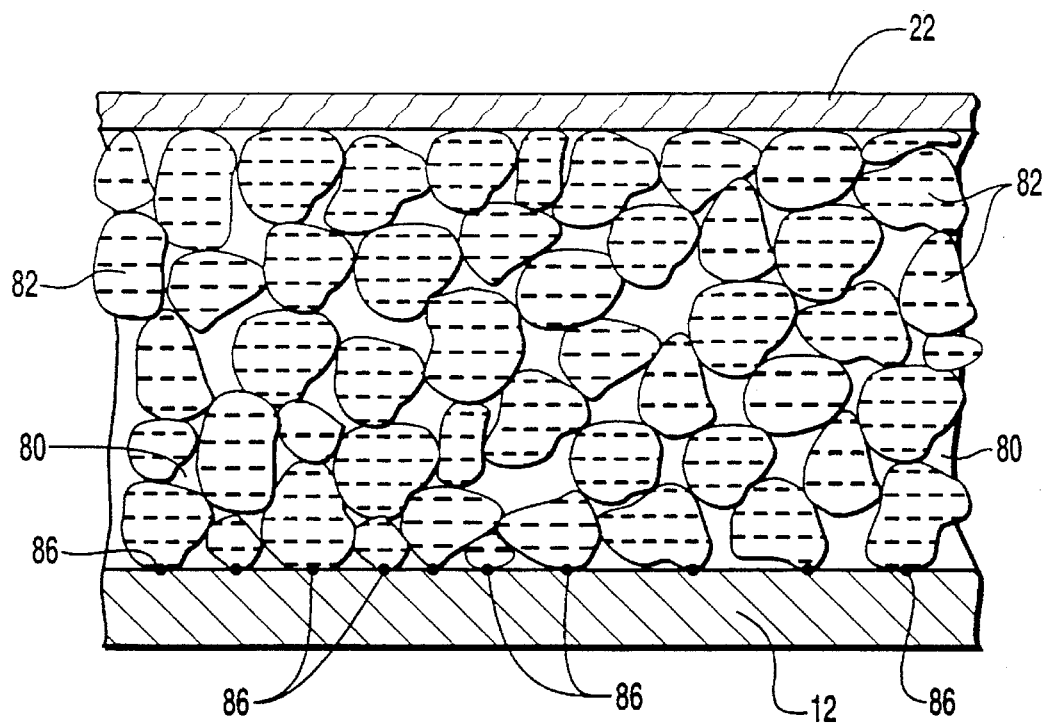

FIG. 9 shows an electrically conductive electrode in amplified view of the materials therein, having a current collector, electron conductive phases, gas phases, three-phase contact areas, and a protonic conductive membrane.

Figure 10:
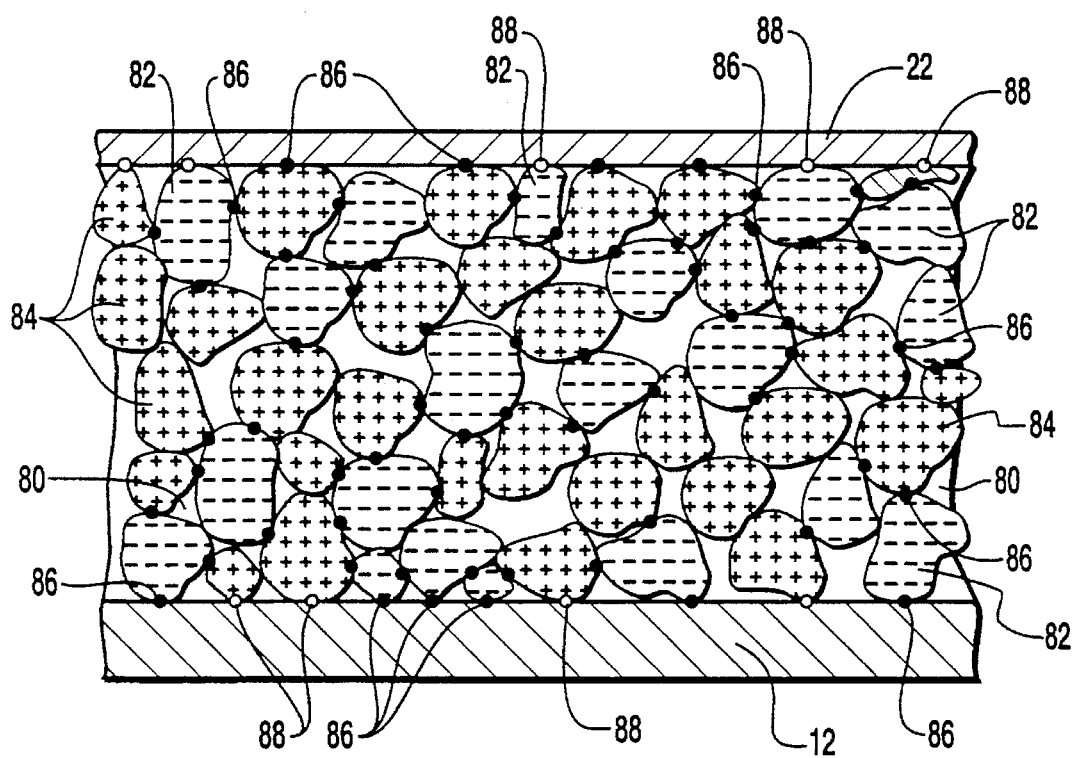

FIG. 10 shows a mixed protonic-electronic conductive electrode in amplified view of the materials therein having a current collector, protonic and electronic conductive phases, gas phases, three-phase contact areas, and a protonic conductive membrane.

Figure 11:
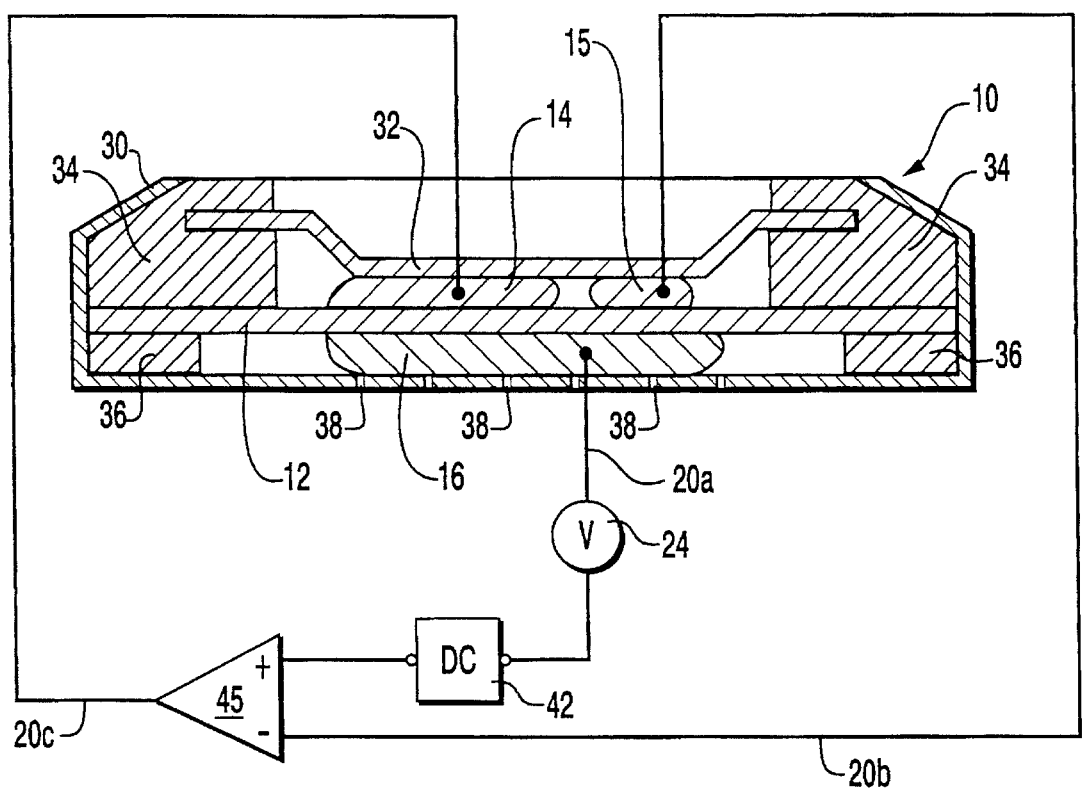

FIG. 11 is an alternative embodiment of the inventive gas sensor having three electrodes which are a sensing electrode, a counter-electrode, and a counter electrode.

DETAILED DESCRIPTION OF THE PREFERRED EMBODIMENTS

The inventive CO sensor is a solid proton conductor room temperature having a fast and high signal response. To achieve a fast detection time and a high signal response, it is desirable to provide a CO sensor having a low bulk ionic resistance. Bulk ionic resistance $R_{bulk}$ of the inventive sensor is equal to $$R_{bulk} = R_o \frac{d}{s} \quad (3)$$

where $R_o$ is the ionic resistivity of the protonic conductive membrane, S is the cross section area of the protonic conductive membrane between the two electrodes, and d is the thickness of the protonic conductive membrane.

Resistance of an electrochemical cell includes at least three components: 1) bulk ionic resistance of the membrane, 2) interface resistance between the membrane and electrodes, and 3) electronic resistance of the electrodes. The bulk ionic resistance of the sensor is reduced to about 1 ohm by the inventive button sensor design, such that R bulk is not a performance limit. Electronic resistivity of the electrodes is in order of 10–5 ohm.cm and obviously is not a performance limit. Therefore, the interface resistance, which is relative to the available three-phase contact area, becomes the performance limit.

Assuming that a button NAFION$^{TM}$ CO sensor is exposed to 1,000 ppm CO with air. The Nernst Potential of the sensor is about 200 mV according to our experiment data. If the interface resistance is insignificant, the response shorting current would be about 200 mA (or 250 mA/cm$^2$). For the real case, we only recorded a response current less than 1 mA/cm$^2$ due to existing a large interface resistance. The interface resistance of the sensor according to this invention has been reduced by introducing our mixed proton-electronic conductor.

Two alternative embodiments of the inventive CO sensor are depicted in FIG. 2 as button sensor 10. Button sensor 10 has a protonic conductive membrane 12 situated between counter electrode 14 and sensing electrode 16. Button sensor 10 has a "button" shape due to a metal can having an opening which is covered by a metallic cap 32. Can 30 has air sampling holes 38 therein so as to provide a venting of sensing electrode 16 to the ambient. An insulation packing material 34 electrically insulates cap 32 from can 30. A washer 36 separates protonic conductive membrane 12 from can 30. A voltage meter 44 measures potential differences between electrical leads 20, 22 in a potentiometric CO gas sensor embodiment.

Figure 1:
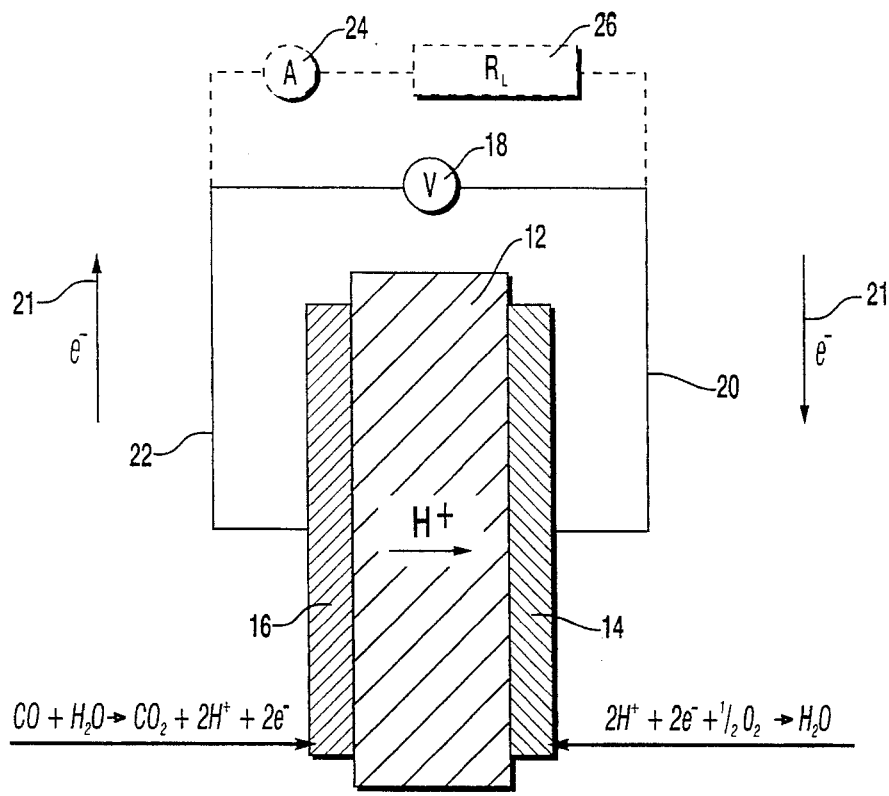
FIG. 1 is an electrochemical gas sensor showing the transport processes of both a potentiometric CO sensor and an amperometric CO sensor, where hydrogen protons are conducted through a protonic conductive membrane situated between sensing and counter electrodes, where electrons travel between said electrodes away from the protonic conductive membrane, where the sensing electrode is the locus of the oxidation reaction of carbon monoxide instigated by a catalyst, and the counter electrode is the locus of the synthesis of water from the products of the electrochemical reaction of the sensor.

In a second embodiment shown in FIG. 2, electrical leads 20, 22 are connected to a switching mechanism for button sensor 10 made up of a switch 40 that is opened and closed by unit 42 so as to alternatively provide a power source 44 in electrical communication with cap 32 and can 30 of button sensor 10. The purpose of the foregoing electrical switching circuitry is to provide a switchable CO pump to button sensor 10 so as to direct CO away from counter electrode 14 before and after sensing and measuring CO concentration with button sensor 10. Alternative, as shown in connection with FIG. 1, an amp meter 24, in combination with a resistor $R_L$ 26 provides an amperometric CO sensor embodiment when button sensor 10 of FIG. 2 incorporates the circuitry seen in FIG. 1. If switchable CO pump circuitry is not included in the embodiment of button sensor 10 shown in FIG. 2, then continuous sensing without CO pumping is performed by button sensor 10.

The amperometric sensor also can be combined with an electrochemical CO pump, as defined hereinafter, and accurate response will be achieved in such combined sensors. In the inventive button sensor design as shown in FIG. 2, it is desirable that both area and thickness parameters are optimized. It is beneficial for button CO sensor 10 to have a 0.1 mm–1 mm thick NAFION$^{TM}$ protonic membrane, and that the diameter of sensing and counter electrodes 16, 15 be approximately 1 mm to 15 mm. Preferably, button CO sensor 10 has a 0.17 mm thick NAFION$^{TM}$ protonic membrane or the like with 10 mm diameter sensing and counter electrodes 16, 14, which results in a bulk ionic resistance of 1.0 ohm. The proton conductor for both the sensing and counter electrodes is preferably a copolymer based on a tetrafluorethylene backbone with a side chain of perfluorinated monomers containing sulfonic or carboxyic acid groups, especially a NAFION$^{TM}$ 117 material from Du Pont, a R4010 or a R1010 material form Pall RAI Manufacture Co., or the like.

Protonic conductors membranes are usually slightly permeable to CO gas. When a membrane is under a carbon monoxide partial pressure difference, a very small amount of carbon monoxide will permeate across the membrane into the counter electrode side.

Influence of the CO permeation to sensor response usually is insignificant because this very small amount of permeated CO is instantly converted into carbon dioxide at the reference electrode. If a precision CO concentration detection is needed, CO concentration in the counter electrode can be minimized by attaching an electrochemical CO pump to the sensor according to this invention. The purpose of an electrochemical pumping circuitry is to prevent the buildup of CO gas at the counter electrode side of the sensor so that a precision CO detection is achieved.

Protonic conductive membrane 12 may be substantially composed of a solid, perfluorinated ion-exchange polymer, or a metal oxide protonic conductor electrolyte material. The following table serves as a further example of solid state protonic conductor which can be used at room temperature in the inventive gas sensor.

| MATERIALS | | |
|---|---|---|
| 1. $H_3Mo_{12}PO_{40}.29H_2O$ | 6. NAFION ™ | DuPont.(US) |
| 2. $H_3W_{12}PO_4.29H_2O$ | 7. C membrane | Chlorine Engineer's (Japan) |
| 3. $HUO_2PO_4.4H_2O$ | 8. XUS-1304.10 | Dow (US) |
| 4. $Zr(HPO_4)_2.3H_2O$ | 9. R4010-55 | PALL RAI Manufacturing Co. (US) |
| 5. $Sb_2O_5.4H_2O$ | | |

Protonic conductive membrane 12 is preferably constructed of materials 6, 7, 8, or 9 which are unreinforced film of perfluorinated copolymers.

FIGS. 3A and 3B show the alterative operation of an electrochemical CO pump and CO sensor response, the circuitry for which is depicted in FIG. 2. A DC pulse power is applied across protonic conductive membrane 12 seen in FIG. 2. This DC pulse power pump voltage is seen in FIG. 3A at counter line 62 showing a 2 V voltage, and the sensor response is seen by counter line 68 in FIG. 3B. FIG. 3B indicates that the sensor of output is off during the DC pulse power application to protonic conductive membrane 12. During the electrochemical CO pump process, permeated CO gas is catalytically converted to protons, which are then pumped out of the side of button sensor 10 associated with reference electrode 14. counter line 64 in FIG. 3A shows no pump voltage applied to membrane 12, and counter line 70 in FIG. 3B shows the sensor output reading of button sensor 10 when the electrochemical CO pump is not active.

As seen in FIG. 3A, a pump voltage of 2 V is preferred for the electrochemical CO pump stage. The pump voltage applied in FIG. 3A and the sensor output reading voltage seen in FIG. 3B are representative of the intermittent sensor output and electrochemical CO pumping operational capabilities of button sensor 10 seen in FIG. 2.

FIG. 4 features counter numerals similar to FIG. 2, with identical counter numerals referring to similar structures performing similar functions. FIG. 4 shows an alternative embodiment of button sensor 10, which lacks the DC power switching circuitry shown in FIG. 2, but includes pumping electrodes 15, 17 interfacing protonic conductive membrane 12. The purpose of pumping electrodes 15, 17 is to continuously pump CO away from counter electrode 14 side of button sensor 10 while continuously sensing the presence of CO gas in the ambient. This continuous pumping of CO away from the side of button sensor 10 where counter electrode 14 is located serves to give stability to the sensor signal response to CO concentration in the ambient. The DC power source can be operated in either "pulse" mode to pump CO, or in the "on" mode to sense CO concentration. In button sensor 10, depicted in FIG. 4, both can 30 and cap 32 are preferably made of electrically insulative materials.

A further embodiment of the inventive CO sensor is seen in FIG. 5 as a button sensor 110. Button sensor 110 has two protonic conductive membranes that prevent interference with button sensor 110's response to the detection of CO concentrations. Button sensor 110 features a metallic shell 130 having a porous centerpiece 135 terminated at either end thereof by walls having a concave configuration. A bottom cap 132A and a top cap 132B are both porous, respectively having holes 138A, 138B therethrough, and being comprised of a metallic substance, preferably similar to can 130. Insulation material 134 insulates a first protonic conductive membrane 122 and a second protonic conductive membrane 112. Washer 136 separates porous centerpiece 135 from first and second protonic conductive membranes 122, 112. A sensor electrode 116 is on an opposite side of first protonic conductive membrane 122 from a counter electrode 114. Counter electrode 114 contacts with metallic centerpiece 135 of can 130. Pumping electrodes 115, 117 are in contact with opposite sides of second protonic conductive membranes 112.

A DC power source 140 is in electrical contact with pumping electrode 115 and metallic can 130 through electrical contacts 146 and 144. Sensing electrode 116 is in contact with an electrical measurement means 142 through electrical leads 148, 144. DC power supply 140 serves as a CO pump to button sensor 110. Electrical sensing means 142 is used to measure the response of button sensor 110 to concentrations of CO.

Sensing electrode 116 is exposed to the ambient through holes 138A.

CO pumping electrode 115 is exposed through holes 138B to a sealed chamber 115A which serves as a counter environment.

Sensing electrode 116 is exposed to the ambient through holes 138A. First protonic conductive membrane 122 performs the function, in combination with counter and sensing electrodes 114, 116, of sensing CO concentration through the conduction therethrough of protons. Second protonic conductive membrane 112, in combination with pumping electrodes 115, 117, performs the function of pumping CO out of the side of button sensor 110 associated with counter electrode 114 so as to stabilize the sensor response of button sensor 110 upon the detection of a concentration of CO in the ambient.

FIG. 6A shows the results of five different embodiments of the inventive CO sensor. As can be seen by FIG. 6A, current responds linearly in a logarithmic scale to ambient concentration of CO. FIG. 6A also shows that increasing concentrations of methane and propane do not interfere with CO sensing of the inventive sensor.

FIG. 6B shows sensor voltage response with respect to time of the inventive two protonic conductive membrane gas sensor seen in FIG. 5. Reference point 90 shows zero time with a CO concentration of 1–2 ppm. Reference point 92 shows an environment of 5–10 ppm CO after a period of 1,000 minutes. At reference point 92 on FIG. 6B, an injection of 100 ppm CO is made into the environment such that sensor response maximizes at reference point 94 on FIG. 6B. At reference point 94 on FIG. 6B, the atmosphere is seen to be opened up to clean air and the sensor response decreases to reference point 94A on FIG. 9B after a period of 3 minutes. At reference point 95 on FIG. 6B, background CO concentration rises from 15–20 ppm until sensor response maximizes at reference point 96 on FIG. 6B. Clean background air is introduced into the environment at reference point 96 on FIG. 6B such that sensor response declines to reference point 98 on FIG. 6B. FIG. 6B reflects environmental parameters of 19°–24° C. and 23–29% relative humidity. Such a sensor voltage response is seen in a nonlogrithmic scale in FIG. 6B.

FIG. 7 shows the voltage response of the inventive sensor to changes in the atmospheric concentration of CO, where a response of 120 mV is seen at counter point 72 in a concentration of 500 ppm CO, which response required 10 seconds to achieve from reference point 70 where an insignificant concentration of CO was present in the ambient. The sensing electrode was exposed to an environment containing CO, whereas the counter electrode side was exposed to clean air. As can be seen from FIG. 7, the inventive CO sensor has a rapid response time in comparison to prior art CO sensors.

FIG. 8 shows the characteristic of the inventive CO sensor with respect to its independence of varying relative humidity environments. In a potentiometric embodiment of the inventive CO gas sensor, as can be seen from FIG. 8, relative humidity does not interfere with the linear nature of the sensor response in increasing environments of CO concentration.

The ability of the inventive CO sensor to avoid interference with relative humidity is that, with increased relative humidity, bulk ionic resistance of the inventive CO sensor goes down as current flow increases. The resistance decrease and current increase are proportionally the same. Thus, voltage, or sensor response, remains constant as evidenced by the equation V=RI.

In the inventive CO sensor, the sensing electrode is exposed to an environment containing CO, whereas the counter electrode side is sealed air-tight. The sensing mechanism of this sensor is essentially the same as that of the sensor with an opened reference electrode. The protonic conductive membrane can be as thin as 0.2 mm so that the reactant oxygen and the produced water permeate the membrane. A small part of CO gas also permeates through the membrane, but the permeated CO is consumed by the reaction with oxygen electrochemically and catalytically at the counter electrode.

FIG. 9 is an amplified view of an electrically conductive electrode having protonic conductive membrane 12, a current collector electrical lead 22, and an electron conductive phase material 82 therebetween. Electron conductive phase material 82 has a plurality of gaps 80 interstitially placed between particles of electron conductive phase material 82. A plurality of three-phase contact areas 86 exists and interfaces between protonic conductive membrane 12 and electron conductive phase material 82. CO gas in the ambient coming in contact with electron conductive phase material 82 produces electrons which are drawn to current collector electrical lead 22. CO gas in the ambient coming in contact with the interface of electron conductive phase material 82 and protonic conductive membrane 12 at three-phase conductive contact area 86 will produce hydrogen ions, or protons, which are conducted through protonic conductive membrane 12. As can be seen from FIG. 9, the creation of hydrogen ions occurs only at the surface of protonic conductive membrane 12 at three-phase contact area 86. Thus, there is limited surface at which the creation of hydrogen ions can take place in the embodiment of the electronically conducted electrode shown in FIG. 9.

FIG. 10 shows a mixed protonic-electronic conductive electrode having a protonic conductive membrane 12, a current collector electrical lead 22, and a variety of amplified particles therebetween and consisting of an electronic conductive phase material 82, and a protonic conductive phase material 84. Between particles of protonic conductive phase material 84 and electronic conductive phase material 82, there are gaps 80 which represent the pores between the particles situated between current collector electrical lead 22 and protonic conductive membrane 12. Electrons are transmitted to current collector electrical lead 22 when CO gas in the ambient comes in contact with three-phase contact area 86. Hydrogen ions are transported to protonic conductor membrane 12 when CO gas in the ambient comes in contact with three-phase contact area 86. The creation of both hydrogen ions and electrons occurs at each of the plurality of three-phase contact areas 86 shown in FIG. 10. Neither electrons nor hydrogen ions are created at interface 88 which is situated between protonic conductive membrane 12 and protonic conductive phase material 84. Similarly, no reaction to create electrons or hydrogen ions occurs at an interface 88 between current collector electric lead 22 and electronic conductor phase material 82.

As can be seen from FIG. 10, the creation of hydrogen ions occurs in the three-dimensional area between current collector electrical lead 22 and protonic conductive membrane 12. Thus, the surface area available to create hydrogen ions is greater in the electrodes seen in FIG. 10 as compared to the electrode seen in FIG. 9. This additional surface area for creation of hydrogen ions is due to the presence of protonic conductive phase material 84 in the electrode above protonic conductive membrane 12. Conversely, FIG. 9 does not contain any protonic conductive phase material situated on and above protonic conductive membrane 12.

The mixed conductor material found in the electrode seen in FIG. 10, by providing a high surface area for the CO oxidation reaction in the sensing electrode side, produces a faster and more sensitive sensor response than the electrode seen in FIG. 9.

The mixed conductor material found in the electrode seen in FIG. 10, by providing a high surface area for the $H_2O$ formation reaction in counter electrode side, produces a faster and more sensitive sensor response than the electrode seen in FIG. 9.

FIG. 11 depicts an embodiment of the inventive sensor having three electrodes. While the foregoing embodiments of the inventive sensor used only two electrodes, and thereby resulted in cost savings, a three-electrode embodiment of the invention is seen as button sensor 10 in FIG. 11. Counter numerals in FIG. 11 identical to counter numerals in FIG. 2, represent similar structures performing similar functions.

Button sensor 10 in FIG. 11 has a counter electrode 14, and a reference electrode 15 between an electrical insulation cap 32 and a protonic conductive membrane 12. On an opposite side of protonic conductive membrane 12 is a sensing electrode 16. Sensing electrode 16 is vented to the ambient through holes 38 on a bottom side of can 30. Gasket 36 and insulation material 34 keep counter electrode 14 and reference electrode 15 air tightly sealed.

Electrical lead 20A electrically contacts sensing electrode 16 through can 30. Electrical lead 20A is connected to an amp meter 24 which is in series with a DC power source 42. DC power source 42 is connected to amplifier 45, which amplifier 45 is connected through to electrical lead 20B, which penetrates cap 32 into counter electrode 14. Amplifier 45 is electrically connected to an electrical lead 20C which penetrates through can 30 into counter electrode 14. The function of the electrical circuitry shown in FIG. 11 is to set the electrical potential of sensing electrode 16 to a given constant value with respect to reference electrode 15. Although potential differences exist between sensing electrode 16 and reference electrode 15, there is no current flowing therebetween. At the same time, the electrical current passing between sensing electrode 16 and counter electrode 14, which is indicative of CO concentration, is recorded by amp meter 24.

The inventive CO gas sensor using the mixed protonic-electronic conductive materials in the electrodes with high surface area of 100 to 1000 $M^2/g$ shows a shorting current as high as 150 $\mu A/cm^2$ to 1,000 ppm CO, which is at least two orders of magnitude higher compared to the sensors with electronic conductive electrodes according to prior art. A preferred composition of such electrodes is as follows:

| COUNTER ELECTRODE | SENSING ELECTRODE |
|---|---|
| 7.5 wt % Ru oxide | 20 wt % Pt-black |
| 67.5 wt % carbon | 55 wt % carbon |

-continued

| COUNTER ELECTRODE | SENSING ELECTRODE |
|---|---|
| 25 wt % NAFION ™ | 25 wt % NAFION ™ |

Other compositions of such electrodes are as follows:

| COUNTER ELECTRODE | SENSING ELECTRODE |
|---|---|
| Pd 20 wt % | Pd 20 wt % |
| Carbon 60 wt % | Carbon 60 wt % |
| $Sb_2O_5.4H_2O$ 20 wt % | $Sb_2O_5.4H_2O$ 20 wt % |
| Rb 25 wt % | Pd 25 wt % |
| Carbon 50 wt % | Ni 50 wt % |
| R4010-55 25 wt % | R4010-55 25 wt % |
| 10 wt % Pt on vulcan carbon | 10 wt % Pt on vulcan carbon |
| XC72 25 wt % | XC72 25 wt % |
| NAFION ™ 25 wt % | NAFION ™ 25 wt % |
| Ti 50 wt % | Ni 50 wt % |
| 20 wt % Pt-Black | 20 wt % Pt-black |
| 55 wt % carbon | 55 wt % carbon |
| 25 wt % NAFION ™ | 25 wt % NAFION ™ |

The role of platinum in the sensing electrode is to favor the CO decomposition reaction (1) whereas Ru oxide in the counter electrode is to favor the water formation reaction (2). According to this invention, the Ru oxide, instead of expensive platinum and the like, as reported in prior art, shows excellent CO sensing performance.

It is also contemplated that the electrodes disclosed herein can be composed substantially of carbon, noble metals, or conductive metal oxides. The electrical conducting material in electrodes disclosed here is preferably a proton-electron mixed conductive material having 10–50 wt% of a proton conductor material and 50–90 wt% of a first and a second electrical conductor material. The proton conductor material for the electrodes disclosed herein is preferably a copolymer having a tetrafluorethylene backbone with a side chain of perfluorinated monomers containing at least one of a sulfonic acid group or carboxylic acid group. Preferably, one of the first and second electrical conductor materials for the sensing electrodes disclosed herein is 50–99 wt% of carbon black, and the other of the first and second electrical conductor materials for the sensing electrodes disclosed herein is 1–50 wt% of platinum. Also preferably, one of the first and second electrical conductor materials for the counter electrode is 50–99 wt% of carbon black, and the other of the first and second electrical conductor materials for the counter electrode is 1–50 wt% of Ru oxide.

In a composition of 25 wt% protonic conductor in electrodes, which is a physically continuous phase, there is proton conduction, whereas the rest of the phases in electrodes provide electronic conduction as well as catalytic activity. If without 25 wt% proton conductor in electrodes, the electrodes were only an electronic conductor, and the reactions (1) and (2), above, would only occur at three-phase contact area 86 seen in FIG. 9, which is a very limited small area. When the electrodes are made of mixed conductors according to this invention, the reactions (1) and (2) will occur on all surface of the electrodes. Therefore, by using high surface area mixed conductive electrodes (100 to 1,000 $M^2/g$) seen in FIG. 10, fast CO reaction kinetics at the interface are achieved and strong signal response is obtained.

While the inventive gas sensor can be used to measure CO concentration, it is also capable of measuring other gases such as $H_2$, $H_2S$, $H_2O$ vapor, and $NO_x$ concentrations.

Various protonic conductors, including organic protonic conductors and inorganic protonic conductors, can be used in the sensor according to this invention. In what follows, a copolymer protonic conductive membrane based on a tetrafluoroethylene backbone with a side chain of perfluorinated monomers containing sulfonic acid group is used herein as an example of the fabrication of the inventive sensor.

To prevent deterioration of the polymer membrane in the subsequent wetting/drying steps, the membrane must be first converted from the proton form to the sodium form by the following steps A:

A. The polymer membrane is soaked in lightly boiling dilute NaOH solution for 1–3 hours. It is then rinsed first in tap water for 0.5–3 hours, then in deionized water for 10–30 minutes, and is then laid out on a rack to air dry.

B. The materials for the preferred mixed conduction electrodes are as follows: Pt/carbon powder, carbon powder, Ru oxide powder, solubilized polymer solution, Glycerol, NaOH solution, and deionized water.

C. The steps for fabrication are as follows:
  1. Pre-mix deionized water and glycerol in 20–30% weight ratio, and store the mixture in a container;
  2. Weigh an appropriate amount of Pt/carbon powder into a clean container;
  3. Weigh an appropriate amount of 5%wt polymer solution, and add to material in step C.2, and then mix. Typically, add 1–3 parts 5%wt $NAFION^{TM}$ solution (on a dry polymer basis) to 3–5 parts Pt/carbon powder;
  4. Weigh and add an appropriate amount of water/glycerol mixture to mixture in step C.3, and then mix. Typically, add 25–35 parts water/glycerol mixture to one pan Pt/carbon powder;
  5. Weigh and add an appropriate amount of 1–2 Moles NaOH to the mixture in step C.4, and then mix. Typically, add 1–2 parts 1–2 Moles NaOH to 9–15 parts 5%wt polymer solution; and further mix the wet electrode mixture ultrasonically for 60 minutes.

D. For Carbon/Ru Oxide electrode preparation, the following steps are taken:
  1. Pre-mix the deionized water and glycerol in 20–30% weight ratio, store the mixture in a container, and set aside;
  2. Weigh an appropriate amount of carbon powder and Ru oxide into a clean container;
  3. Weigh an appropriate amount of 5%wt polymer solution, and add to the material in step D.2, and then mix. Typically, add 1–3 parts 5%wt polymer solution (on a dry polymer basis) to 3–5 parts carbon/Ru oxide powder;
  4. Weigh and add an appropriate amount of water/glycerol mixture to mixture in step D.3, and then mix. Typically, add 25–35 parts water/glycerol mixture to 1 part carbon/Ru oxide powder;
  5. Weigh and add an appropriate amount of 1–2 Moles NaOH to the mixture in step C.4, and then mix. Typically, add 1 part 1–2 Moles NaOH to 9–15 parts 5%wt polymer solution; and further mix the wet electrode mixture ultrasonically for 60 minutes.

E. For Pt/Carbon Electrode application drying, the following steps are taken:
  1. Re-mix the wet electrode mixture ultrasonically for at least 30 minutes prior to use;
  2. Fill the dispensing machine tubing with the Pt/carbon wet electrode mixture;
  3. Dispense the wet electrode mixture to the surface of the membrane at the desired location; and 4. Place the membrane/electrode in an oven at 100°–170° C. for 10–60 minutes.

F. For Carbon/Ru Oxide Electrode application drying, the following steps are taken:

Repeat step A on the opposite side of the membrane.

G. For acidification, the following steps are taken:
1. For Ion-Exchange, soak membrane/electrodes in lightly boiling dilute MH2S04 solution for 1–3 hours.
2. For cleaning, rinse the membrane/electrodes in deionized water;
3. For drying, dry the membrane/electrodes in air, or air dry then desiccate overnight, or place in a 30°–50° C. oven for 1–3 hours before cutting to the final dimensions.

The present invention may be embodied in other specific forms without departing from its spirit or essential characteristics. The described embodiments are to be considered in all respects only as illustrated and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. An electrochemical gas sensor for quantitative measurement of a gas in an ambient atmosphere comprising:

a porous mixed ionic-electronic conductive sensing electrode having both an electronic conducting material and an ionic conducting material;

a porous mixed ionic-electronic conductive counter electrode having both an electronic conducting material and an ionic conducting material;

a first protonic conductive electrolyte membrane in between and in contact with the sensing and counter electrodes, and having a thickness in the range of approximately 0.1 mm to 1 mm;

the sensing electrode reacting with the gas to produce a change in an electrical characteristic between the sensing electrode and the counter electrode;

means for electrical measurement;

said sensing and counter electrodes each having a diameter in the range of approximately 1 mm to 15 mm, and being electrically connected to said electrical measurement means;

whereby, in a positive ambient concentration of said gas, said electrical measurement means detects changes in said electrical characteristic.

2. The electrochemical gas sensor as defined in claim 1, further comprising:

means for applying DC power across the protonic conductive electrolyte membrane;

an electrical connection between the sensing electrode, the counter electrode, and the means for applying DC power across the protonic conductive electrolyte membrane; and switch means for alternating an electrical connection between the sensing electrode and counter electrode from the electrical measurement means to the means for applying DC power across the protonic conductive electrolyte membrane;

whereby the gas is transported away from the counter electrode when the means for applying DC power across the protonic conductive electrolyte membrane applies a DC power to the sensing and counter electrodes.

3. The electrochemical gas sensor as defined in claim 1, wherein said sensing and counter electrodes comprise carbon.

4. The electrochemical gas sensor as defined in claim 1, wherein said sensing and counter electrodes comprise noble metals.

5. The electrochemical gas sensor as defined in claim 1, wherein said sensing and counter electrodes comprise conductive metal oxides.

6. The electrochemical gas sensor as defined in claim 1, wherein the protonic conductive electrolyte membrane is substantially comprised of a solid, perfluorinated, ion-exchange polymer.

7. The electrochemical gas sensor as defined in claim 1, wherein the protonic conductive electrolyte membrane is a metal oxide protonic conductor electrolyte membrane.

8. The electrochemical gas sensor as defined in claim 1, wherein the electrochemical gas sensor is adapted to detect CO.

9. The electrochemical gas sensor as defined in claim 1, wherein the electrochemical gas sensor is adapted to detect $NO_x$.

10. The electrochemical gas sensor as defined in claim 1, wherein the electrochemical gas sensor is adapted to detect hydrogen.

11. The electrochemical gas sensor as defined in claim 1, wherein the electrochemical gas sensor is adapted to detect $H_2S$.

12. The electrochemical gas sensor as defined in claim 1, wherein the electrochemical gas sensor is adapted to detect $H_2O$ vapor.

13. The electrochemical gas sensor as defined in claim 1, wherein the sensing and counter electrodes have a diameter of about 10 mm, and the protonic conductive electrolyte membrane has a thickness of about 0.17 mm.

14. The electrochemical gas sensor as defined in claim 1, wherein the electronic and ionic conducting materials of said sensing and counter electrodes are a proton-electron mixed conductive material having 10–50 wt% of a proton conductor material and 50–90 wt% of a first and a second electrical conductor materials.

15. The electrochemical gas sensor as defined in claim 14, wherein the proton conductor material for both the sensing and counter electrodes is a copolymer having a tetrafluoroethylene backbone with a side chain of perfluorinated monomers containing at least one of a sulfonic acid group or a carboxylic acid group.

16. The electrochemical gas sensor as defined in claim 14, wherein one of the first and second electrical conductor materials for the sensing electrode is 50–99 wt% of carbon black, and the other of the first and second electrical conductor materials for the sensing electrode is 1–50 wt% of platinum.

17. The electrochemical gas sensor as defined in claim 14, wherein one of the first and second electrical conductor materials for the counter electrode is 50–99 wt% of carbon black, and the other of the first and second electrical conductor materials for the counter electrode is 1–50 wt% of Ru oxide.

18. The electrochemical gas sensor as defined in claim 1, wherein the electrochemical gas sensor further comprises:

first and second porous mixed ionic-electronic conductive pump electrodes each having both an electronic conductive material and an ionic conductive material, each of said first and second pump electrodes being separate from said sensing and counter electrodes and situated on opposite sides of and in contact with said protonic conductive electrolyte membrane;

means for applying a DC power across the membrane;

said first and second pump electrodes having in electrical connection therebetween said means for applying DC power across the membrane;

whereby the gas is transported away from the counter electrode when said means for applying DC power across the membrane applies a DC power to the first and second pump electrodes.

19. The electrochemical gas sensor of claim 18, wherein the electronic and ionic conducting materials of the first and second pumping electrodes comprise carbon.

20. The electrochemical gas sensor as defined in claim 18, wherein the electronic and ionic conducting materials of the first and second pumping electrodes comprise noble metals.

21. The electrochemical gas sensor as defined in claim 18, wherein the electronic and ionic conducting materials of the first and second pumping electrodes comprise conductive metal oxides.

22. The electrochemical gas sensor as defined in claim 18, wherein the first and second pumping electrodes have a diameter of about 10 mm, and the first protonic conductive electrolyte membrane has a thickness of about 0.17 mm.

23. The electrochemical gas sensor as defined in claim 18, wherein the electronic and ionic conducting materials of said first and second pumping electrodes are a proton-electron mixed conductive material having 10–50 wt% of a proton conductor material and 50–90 wt% of a first and a second electrical conductor materials.

24. The electrochemical gas sensor as defined in claim 23, wherein the proton conductor material for both the first and second pumping electrodes is a copolymer having a tetrafluorethylene backbone with a side chain of perfluorinated monomers containing at least one of a sulfonic acid group or a carboxylic acid group.

25. The electrochemical gas sensor as defined in claim 23, wherein one of the first and second electrical conductor materials for the first pumping electrode is 50–99 wt% of carbon black, and the other of the first and second electrical conductor materials for the first pumping electrode is 10 to 50 wt% of platinum.

26. The electrochemical gas sensor as defined in claim 23, wherein one of the first and second electrical conductor materials for the second pumping electrode is 50–99 wt% of carbon black, and the other of the first and second electrical conductor materials for the second pumping electrode is 10 to 50 wt% of Ru oxide.

27. The electrochemical gas sensor as defined in claim 1, wherein the electrochemical gas sensor further comprises:

a second protonic conductive electrolyte membrane;

first and second porous mixed ionic-electronic conductive pump electrodes each having both an electronic conductive material and an ionic conducting material, each of said first and second pump electrodes being separate from said sensing and counter electrodes and situated on opposite sides of and in contact with said second protonic conductive electrolyte membrane;

means for applying a DC power across said second protonic electrolyte membrane;

said first and second pump electrodes having in electrical connection therebetween said means for applying DC power across said second protonic electrolyte membrane;

whereby the gas is transported away from the counter electrode when said means for applying DC power across said second protonic electrolyte membrane applies a DC power to the first and second pump electrodes.

28. The electrochemical gas sensor as defined in claim 27, wherein the second protonic conductive electrolyte membrane is substantially comprised of a solid, perfluorinated, ion-exchange polymer.

29. The electrochemical gas sensor as defined in claim 27, wherein the second protonic conductive electrolyte membrane is a metal oxide protonic conductor electrolyte membrane.

30. An electrochemical gas sensor for quantitative measurement of a gas in an ambient atmosphere comprising:

a porous mixed ionic-electronic conductive sensing electrode having both an electronic conducting material and an ionic conducting material;

a porous mixed ionic-electronic conductive counter electrode having both an electronic conducting material and an ionic conducting material;

a protonic conductive electrolyte membrane in between and in contact with the sensing and counter electrodes;

the sensing electrode reacting with the gas to produce a change in an electrical characteristic between the sensing electrode and the counter electrode;

means for electrical measurement;

said sensing and counter electrodes having electrically connected therebetween said means for electrical measurement;

means for applying a DC pulse power source across the membrane;

said sensing and counter electrodes having in electrical connection therebetween said means for applying DC pulse power across the membrane; and switch means for alternating the connection between the sensing and counter electrodes from the electrical measurement means to the means for applying a DC pulse power source across the membrane;

whereby, in a positive ambient concentration of said gas, said electrical measurement means detects changes in said electrical characteristic when said switch means connects said electrical measurement means to the sensing and counter electrodes; and whereby said means for applying a DC pulse power source across the membrane moves CO away from a side of the gas sensor where the counter electrode is placed when said switch means connects said means for applying a DC pulse power source across the membrane to the sensing and counter electrodes.

31. The electrochemical gas sensor as defined in claim 30, wherein said sensing and counter electrodes comprise carbon.

32. The electrochemical gas sensor as defined in claim 30, wherein said sensing and counter electrodes comprise noble metals.

33. The electrochemical gas sensor as defined in claim 30, wherein said sensing and counter electrodes comprise conductive metal oxides.

34. The electrochemical gas sensor as defined in claim 30, wherein the protonic conductive electrolyte membrane is substantially comprised of a solid, perfluorinated, ion-exchange polymer.

35. The electrochemical gas sensor as defined in claim 30, wherein the protonic conductive electrolyte membrane is a metal oxide protonic conductor electrolyte membrane.

36. The electrochemical gas sensor as defined in claim 30, wherein the electrochemical gas sensor is adapted to detect CO.

37. The electrochemical gas sensor as defined in claim 30, wherein the electrochemical gas sensor is adapted to detect hydrogen.

38. The electrochemical gas sensor as defined in claim 30, wherein the electrochemical gas sensor is adapted to detect $H_2S$.

39. The electrochemical gas sensor as defined in claim 30, wherein the electrochemical gas sensor is adapted to detect $H_2O$ vapor.

40. The electrochemical gas sensor as defined in claim 30, wherein the electrochemical gas sensor is adapted to detect $NO_x$.

41. The electrochemical gas sensor as defined in claim 30, wherein the sensing and counter electrodes have a diameter in a range of 1 mm to 15 mm, and the protonic conductive electrolyte membrane has a thickness in a range of 0.1 mm–1 mm.

42. The electrochemical gas sensor as defined in claim 41, wherein the sensing and counter electrodes have a diameter of about 10 mm, and the protonic conductive electrolyte membrane has a thickness of about 0.17 mm.

43. The electrochemical gas sensor as defined in claim 30, wherein the electronic and ionic conducting materials of said sensing and counter electrodes are a proton-electron mixed conductive material having 10–50 wt% of a proton conductor material and 50–90 wt% of a first and a second electrical conductor materials.

44. The electrochemical gas sensor as defined in claim 43, wherein the proton conductor material for both the sensing and counter electrodes is a copolymer having a tetrafluorethylene backbone with a side chain of perfluorinated monomers containing at least one of a sulfonic acid group or a carboxylic acid group.

45. The electrochemical gas sensor as defined in claim 43, wherein one of the first and second electrical conductor materials for the sensing electrode is 50–99 wt% of carbon black, and the other of the first and second electrical conductor materials for the sensing electrode is 1–50 wt% of platinum.

46. The electrochemical gas sensor as defined in claim 43, wherein one of the first and second electrical conductor materials for the counter electrode is 50–99 wt% of carbon black, and the other of the first and second electrical conductor materials for the counter electrode is 1–50 wt% of Ru oxide.

47. An electrochemical gas sensor for quantitative measurement of a gas in an ambient atmosphere comprising:

a porous mixed ionic-electronic conductive sensing electrode having both an electronic conducting material and an ionic conducting material and being exposed to the ambient atmosphere;

a porous mixed ionic-conductive counter electrode having both an electronic conducting material and an ionic conducting material;

a first protonic conductive electrolyte membrane in between and in contact with the sensing and counter electrodes;

the sensing electrode reacting with the gas to produce a change in an electrical characteristic between the sensing electrode and the counter electrode;

a second protonic conductive electrolyte membrane;

first and second porous mixed ionic-electronic conductive pump electrodes, each having both an electronic conductive material and an ionic conducting material, each of said first and second pump electrodes being separate from said sensing and counter electrodes and situated on opposite sides of and in contact with said second protonic conductive electrolyte membrane;

said first porous pump electrode being exposed to a chamber sealed off from the ambient atmosphere;

said second porous pump electrode being separated from said counter electrode by a perforated support structure composed of an electrical conducting material, both said second porous pump electrode and said counter electrode being in contact with said perforated support structure;

means for electrical measurement in electrical contact with said sensing electrode and perforated support structure;

means for applying a DC power across said second protonic electrolyte membrane in electrical contact with said first pump electrode and said perforated support structure;

whereby the gas is transported away from the counter electrode when the means for applying a DC power across said second protonic electrolyte membrane applies a DC power across said second protonic electrolyte membrane; and whereby, in a positive ambient concentration of said gas, said electrical measurement means detects changes in said electrical characteristic.

48. The electrochemical gas sensor as defined in claim 47, wherein the sensing and counter electrodes have a diameter in a range of 1 mm–15 mm, and the protonic conductive electrolyte membrane has a thickness in a range of 0.1 mm–1 mm.

49. The electrochemical gas sensor as defined in claim 48, wherein the sensing and electrodes have a diameter of about 10 mm, and the protonic conductive electrolyte membrane has a thickness of about 0.17 mm.

50. The electrochemical gas sensor as defined in claim 47, wherein the electronic and ionic conducting materials of said sensing and counter electrodes are a proton-electron mixed conductive material having 10–50 wt% of a proton conductor material and 50–90 wt% of a first and a second electrical conductor materials.

51. The electrochemical gas sensor as defined in claim 50, wherein the proton conductor material for both the sensing and counter electrodes is a copolymer having a tetrafluorethylene backbone with a side chain of perfluorinated monomers containing at least one of a sulfonic acid group or a carboxylic acid group.

52. The electrochemical gas sensor as defined in claim 50, wherein one of the first and second electrical conductor materials for the sensing electrode is 50–99 wt% of carbon black, and the other of the first and second electrical conductor materials for the sensing electrode is 1–50 wt% of platinum.

53. The electrochemical gas sensor as defined in claim 50, wherein one of the first and second electrical conductor materials for the counter electrode is 50–99 wt% of carbon black, and the other of the first and second electrical conductor materials for the counter-reference electrode is 1–50 wt% of Ru oxide.

54. The electrochemical gas sensor as defined in claim 47, wherein the electrochemical gas sensor is adapted to detect CO.

55. The electrochemical gas sensor as defined in claim 47, wherein the electrochemical gas sensor is adapted to detect hydrogen.

56. The electrochemical gas sensor as defined in claim 47, wherein the electrochemical gas sensor is adapted to detect $NO_x$.

57. The electrochemical gas sensor as defined in claim 47, wherein the electrochemical gas sensor is adapted to detect $H_2O$ vapor.

58. The electrochemical gas sensor as defined in claim 47, wherein the electrochemical gas sensor is adapted to detect $H_2S$.

59. An electrochemical gas sensor for quantitative measurement of a gas in an ambient atmosphere comprising:
   a porous mixed ionic-electronic conductive sensing electrode having both an electronic conducting material and an ionic conducting material and being exposed to the ambient atmosphere;
   a porous mixed ionic-electronic conductive reference electrode having both an electronic conducting material and an ionic conducting material;
   a porous mixed ionic-conductive counter electrode having both an electrical conducting material and an ionic conducting material, and being separate from both said sensing and reference electrodes;
   a protonic conductive electrolyte membrane, having top and bottom sides, said top side of said protonic conductive membrane being in contact with the counter electrode and the reference electrode, the bottom side of said protonic conductive membrane being in contact with the sensing electrode;
   the sensing electrode reacting with the gas to produce a change in an electrical characteristic between the sensing electrode and the counter electrode;
   means for electrical measurement in electrical contact between the sensing electrode and the counter electrode;
   means for applying a DC power across said protonic electrolyte membrane in electrical contact between the sensing electrode and said reference electrode;
   whereby the gas is transported away from the reference electrode when the means for applying a DC power across said protonic electrolyte membrane applies a DC power across said protonic electrolyte membrane; and
   whereby, in a positive ambient concentration of said gas, said electrical measurement means detects changes in said electrical characteristic.

60. The electrochemical gas sensor as defined in claim 59, wherein said sensing, count and reference electrodes comprise carbon.

61. The electrochemical gas sensor as defined in claim 59, wherein said sensing, count and reference electrodes comprise noble metals.

62. The electrochemical gas sensor as defined in claim 59, wherein said sensing, counter and reference electrodes comprise conductive metal oxides.

63. The electrochemical gas sensor as defined in claim 59, wherein the protonic conductive electrolyte membrane is substantially comprised of a solid, perfluorinated, ion-exchange polymer.

64. The electrochemical gas sensor as defined in claim 59, wherein the protonic conductive electrolyte membrane is a metal oxide protonic conductor electrolyte membrane.

65. The electrochemical gas sensor as defined in claim 59, wherein the electrochemical gas sensor is adapted to detect CO.

66. The electrochemical gas sensor as defined in claim 59, wherein the electrochemical gas sensor is adapted to detect $NO_x$.

67. The electrochemical gas sensor as defined in claim 59, wherein the electrochemical gas sensor is adapted to detect hydrogen.

68. The electrochemical gas sensor as defined in claim 59, wherein the electrochemical gas sensor is adapted to detect $H_2S$.

69. The electrochemical gas sensor as defined in claim 59, wherein the electrochemical gas sensor is adapted to detect $H_2O$ vapor.

70. The electrochemical gas sensor as defined in claim 59, wherein the sensing, counter and reference electrodes have a diameter of about 10 mm, and the protonic conductive electrolyte membrane has a thickness of about 0.17 mm.

71. The electrochemical gas sensor as defined in claim 59, wherein the electronic and ionic conducting materials of said sensing, counter and reference electrodes are a proton-electron mixed conductive material having 10–50 wt% of a proton conductor material and 50–90 wt% of a first and second electrical conductor materials.

72. The electrochemical gas sensor as defined in claim 71, wherein the proton conductor material for both the sensing, counter and reference electrodes is a copolymer having a tetrafluorethylene backbone with a side chain of perfluorinated monomers containing at least one of a sulfonic acid group or a carboxylic acid group.

73. The electrochemical gas sensor as defined in claim 71, wherein one of the first and second electrical conductor materials for the sensing electrode is 50–99 wt% of carbon black, and the other of the first and second electrical conductor materials for the sensing electrode is 1–50 wt% of platinum.

74. The electrochemical gas sensor as defined in claim 71, wherein one of the first and second electrical conductor materials for the counter and reference electrodes is 50–99 wt% of carbon black, and the other of the first and second electrical conductor materials for the counter and reference electrodes is 1–50 wt% of Ru oxide.

75. The electrochemical gas sensor as defined in claim 1, wherein the sensing and the counter electrodes each have a first side opposite a second side, and wherein the ionic and electronic conducting materials are continuous from the first side to the opposite second side within each of the sensing and counter electrodes.

76. The electrochemical gas sensor as defined in claim 30, wherein the sensing and the counter electrodes each have a first side opposite a second side, and wherein the ionic and electronic conducting materials are continuous from the first side to the opposite second side within each of the sensing and counter electrodes.

77. The electrochemical gas sensor as defined in claim 47, wherein the sensing, counter, first pumping, and second pumping electrodes each have a first side opposite a second side, and wherein the ionic and electronic conducting materials are continuous from the first side to the opposite second side within each of the sensing, counter, first pumping, and second pumping electrodes.

78. The electrochemical gas sensor as defined in claim 59, wherein the sensing, counter, and reference electrodes each have a first side opposite a second side, and wherein the ionic and electronic conducting materials are continuous from the first side to the opposite second side within each of the sensing, counter, and reference electrodes.

\* \* \* \* \*

US005573648C1

(12) EX PARTE REEXAMINATION CERTIFICATE (6069th)
United States Patent
Shen et al.

(10) Number: US 5,573,648 C1
(45) Certificate Issued: Jan. 1, 2008

(54) GAS SENSOR BASED ON PROTONIC CONDUCTIVE MEMBRANES

(75) Inventors: Yousheng Shen, Salt Lake City, UT (US); Franco Consadori, Salt Lake City, UT (US); D. George Field, Pleasant Grove, UT (US)

(73) Assignee: Atwood Industries, Inc., Rockford, IL (US)

Reexamination Request:
No. 90/006,208, Jan. 29, 2002

Reexamination Certificate for:
Patent No.: 5,573,648
Issued: Nov. 12, 1996
Appl. No.: 08/381,718
Filed: Jan. 31, 1995

(51) Int. Cl.
*G01N 27/49* (2006.01)
*G01N 27/407* (2006.01)
*G01N 33/00* (2006.01)

(52) U.S. Cl. .................. 204/412; 204/421; 204/424; 204/425; 204/426; 205/781; 205/783.5; 205/784; 205/786.5; 205/788

(58) Field of Classification Search .................. None
See application file for complete search history.

(56) References Cited

U.S. PATENT DOCUMENTS

| | | | |
|---|---|---|---|
| 3,134,697 A | 5/1964 | Niedrach | |
| 4,227,984 A | 10/1980 | Dempsey et al. | |
| 4,664,757 A | 5/1987 | Zupancic et al. | |
| 4,718,991 A | 1/1988 | Yamazoe et al. | |
| 4,804,592 A | 2/1989 | Vanderborgh et al. | |
| 4,820,386 A | 4/1989 | LaConti et al. | |
| 5,164,053 A | 11/1992 | Razaq et al. | |
| 5,266,421 A | 11/1993 | Townsend et al. | |
| 5,302,274 A * | 4/1994 | Tomantschger et al. | .... 204/412 |
| 5,322,602 A | 6/1994 | Razaq | |
| 5,330,860 A | 7/1994 | Grot et al. | |
| 5,474,857 A | 12/1995 | Uchida et al. | |
| 5,573,648 A | 11/1996 | Shen et al. | |
| 5,650,054 A | 7/1997 | Shen et al. | |

OTHER PUBLICATIONS

"Nafion Distribution in Gas Diffusion Electrodes for Solid–Polymer–Electrolyte–Fuel–Cell Applications"; Z. Poltarzewski, P. Staiti, V. Alderucci, W. Wieczorek, and N. Giordano; J. Electrochem. Soc. Vo. 139, No. 3, Mar. 1992; pp. 761–765.

"Preparation of High–Platinum–Utilization Gas Diffusion Electrodes for Proton–Exchange–Membrane Fuel Cells"; E. J. Taylor, E.B. Anderson, and N.R.K. Vilambi; Electro-Chemical Society Letters; vol. 139, No. 5, May 1992; pp. L45–L46.

"*Liquid Electrolyte Fuel Cells*"; by B.S. Hobbs, A.D.S. Tantram and R. Chan–Henry; Techniques and Mechanisms in Gas Sensing; by P.T. Moseley, J.O.W. Norris and D.E. Williams; Materials and Manufacturing Technology Division, Harwell; Adam Hilger; 1991 pp. 161–188.

* cited by examiner

*Primary Examiner*—Kaj K. Olsen

(57) ABSTRACT

A low cost room temperature electrochemical gas sensor for sensing CO and other toxic analyte gases has a solid protonic conductive membrane with a low bulk ionic resistance. A sensing electrode and a count counter electrode, which are separated by the membrane, can be made of mixed protonic-electronic conductors. Embodiments of the inventive sensor also include an electrochemical analyte gas pump to transport the analyte gas away from the counter electrode side of the sensor. Analyte gas pumps for the inventive sensor include dual pumping electrodes situated on opposite sides of the membrane, and include a means for applying a DC power across the membrane to the sensing and counter electrodes. Another embodiment of the inventive sensor has first and second solid protonic conductive membranes, one of which has a sensing electrode and a counter electrode separated by the first membrane, and the other of which has dual pumping electrodes situtated on opposite sides of the second membrane.

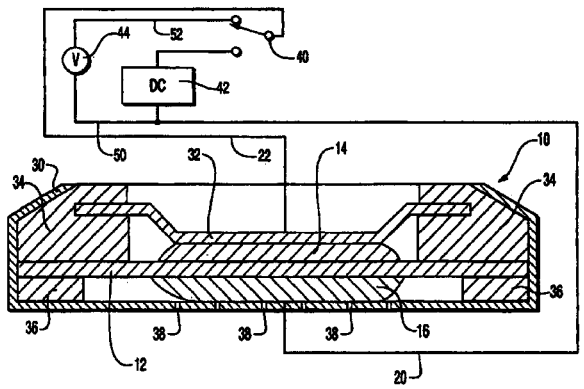

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

The patentability of claims 2, 17–74 and 76–78 is confirmed.

Claims 1, 3–16 and 75 are cancelled.

* * * * *